United States Patent
Nova et al.

(10) Patent No.: US 9,017,272 B2
(45) Date of Patent: Apr. 28, 2015

(54) MEDICAL DEVICE WITH SPEAKER HAVING EXTERIOR DIAPHRAGM

(75) Inventors: Richard C. Nova, Kirkland, WA (US); Robert E. Smith, Lynnwood, WA (US); Gregory V. Browne, Victoria (CA); Ryan D. Lee, Victoria (CA)

(73) Assignee: Physio-Control, Inc., Redmond, WA (US)

( * ) Notice: Subject to any disclaimer, the term of this patent is extended or adjusted under 35 U.S.C. 154(b) by 466 days.

(21) Appl. No.: 13/015,507

(22) Filed: Jan. 27, 2011

(65) Prior Publication Data

US 2012/0071939 A1    Mar. 22, 2012

Related U.S. Application Data

(60) Provisional application No. 61/385,501, filed on Sep. 22, 2010.

(51) Int. Cl.
*A61N 1/39* (2006.01)
*A61H 31/00* (2006.01)

(52) U.S. Cl.
CPC .............. *A61N 1/3968* (2013.01); *A61N 1/3993* (2013.01)

(58) Field of Classification Search
USPC .................................. 607/5, 6–8; 601/41–45
See application file for complete search history.

(56) References Cited

U.S. PATENT DOCUMENTS

| | | | | |
|---|---|---|---|---|
| 6,804,368 B2* | 10/2004 | Tsuda | | 381/415 |
| 2008/0033393 A1* | 2/2008 | Edwards et al. | | 604/503 |
| 2008/0033495 A1* | 2/2008 | Kumar | | 607/5 |
| 2010/0002901 A1* | 1/2010 | Matsuda et al. | | 381/398 |

OTHER PUBLICATIONS

RS-1534A-NL. Technical Datasheet from Regal Electronics. Jul. 12, 2007.*

* cited by examiner

*Primary Examiner* — Allen Porter, Jr.
(74) *Attorney, Agent, or Firm* — Marger Johnson & McCollom PC

(57) ABSTRACT

Embodiments of the present concept are directed to medical devices having features that prevent contaminants from infiltrating the housing of the device while providing a mechanism to provide clear auditory sounds to aid a rescuer in providing care to a patient. In one example, a medical device includes a housing having a transmission area associated with an enclosed voice coil. An exterior diaphragm formed integrally with the housing surrounds the transmission area and provides a watertight seal of the transmission area. In addition, the diaphragm is structured to generate a sound that can be heard by the rescuer from the voice coil.

11 Claims, 5 Drawing Sheets

*EXAMPLE DEVICE WITH EXTERIOR SPEAKER DIAPHRAGM*

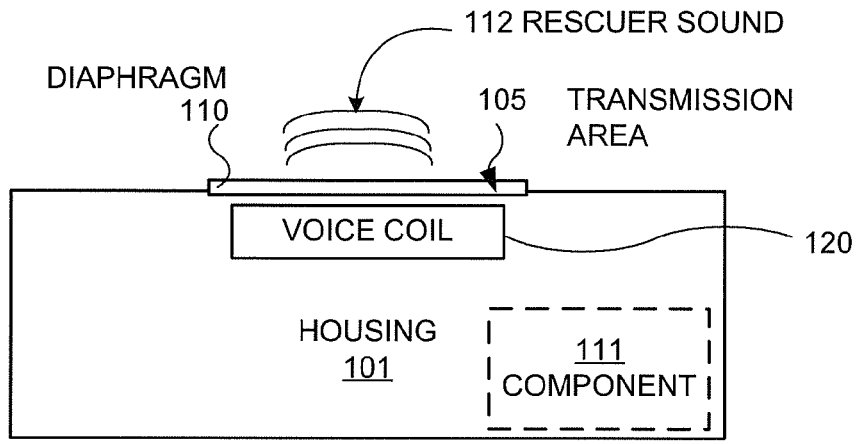
FIG. 1  *DEVICE HOUSING WITH EXTERIOR SPEAKER DIAPHRAGM*
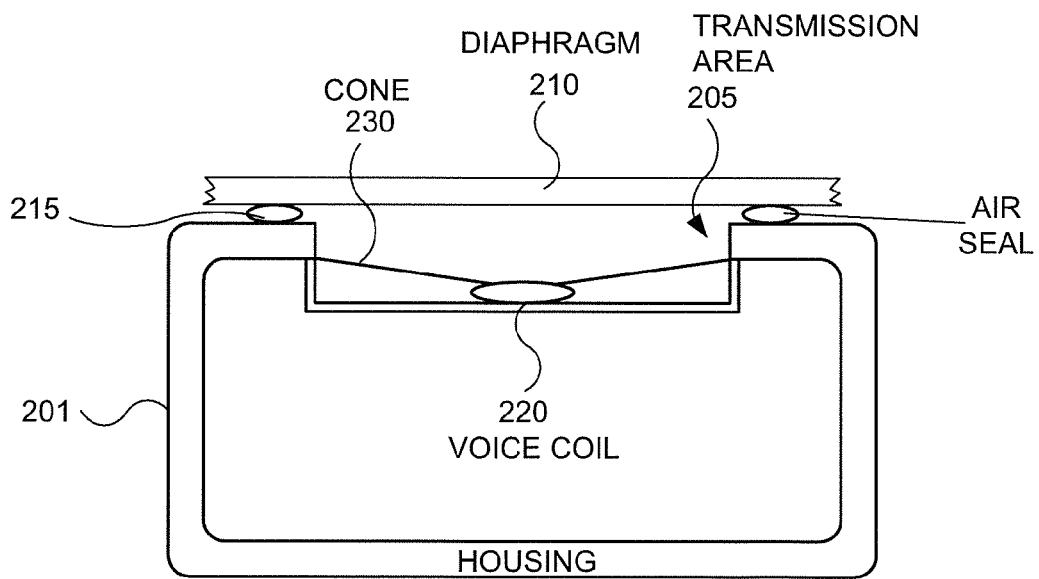
FIG. 2  *EXAMPLE DEVICE WITH EXTERIOR SPEAKER DIAPHRAGM*

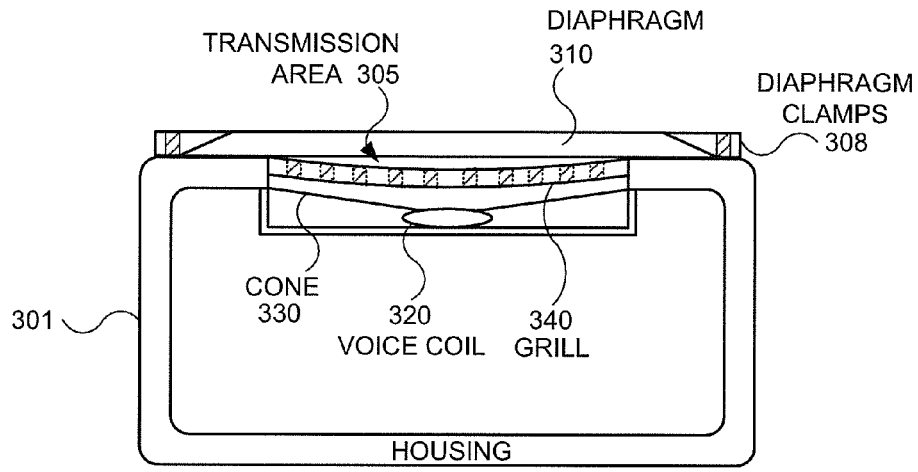
FIG. 3  *EXAMPLE DEVICE WITH EXTERIOR SPEAKER DIAPHRAGM*
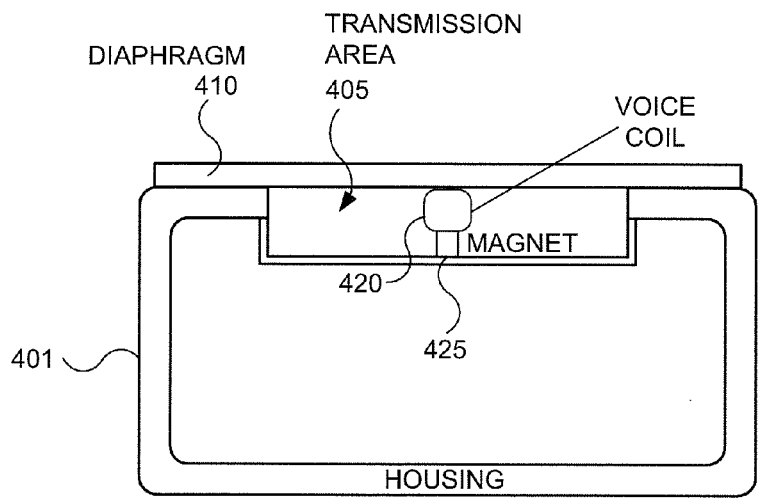
FIG. 4  *EXAMPLE DEVICE WITH EXTERIOR SPEAKER DIAPHRAGM*

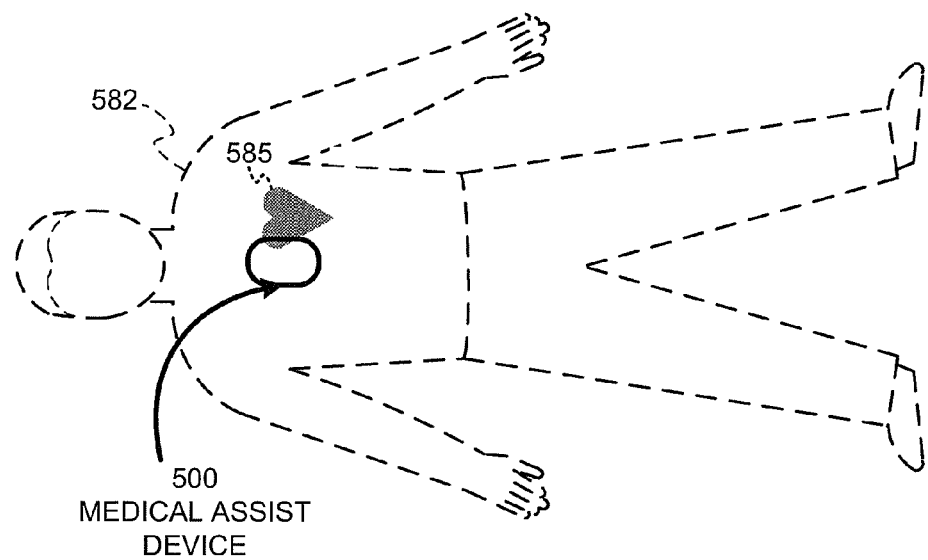
FIG. 5  *MEDICAL ASSIST SCENE*
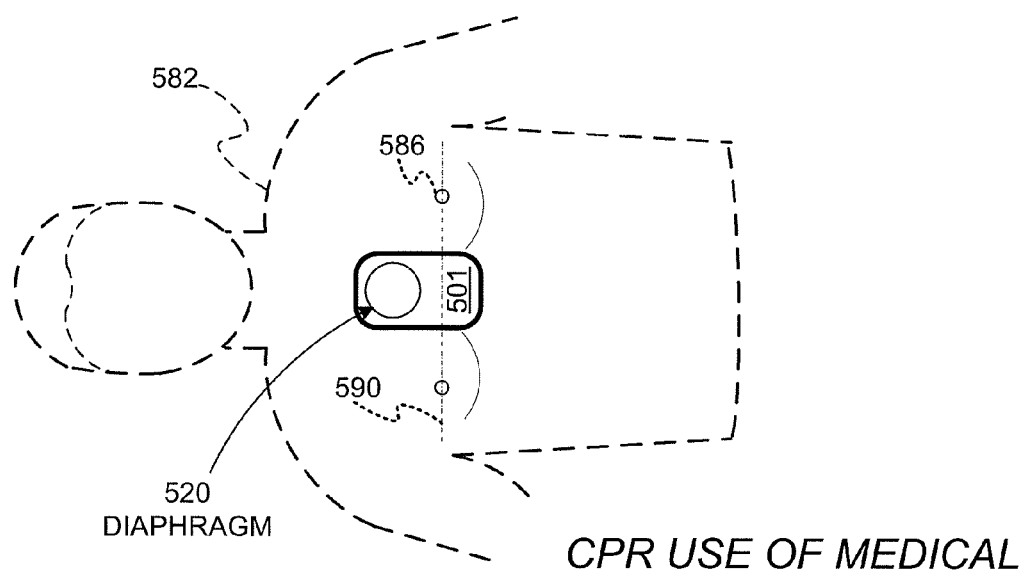
FIG. 6  *CPR USE OF MEDICAL ASSIST DEVICE*

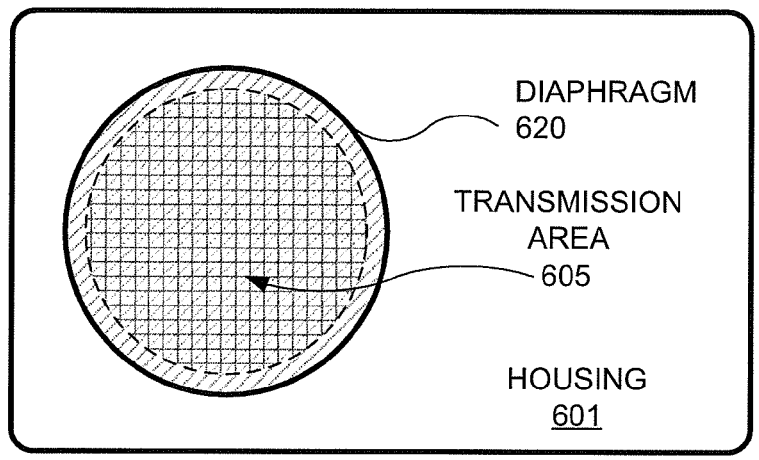
FIG. 7  *MEDICAL ASSIST DEVICE DETAIL*
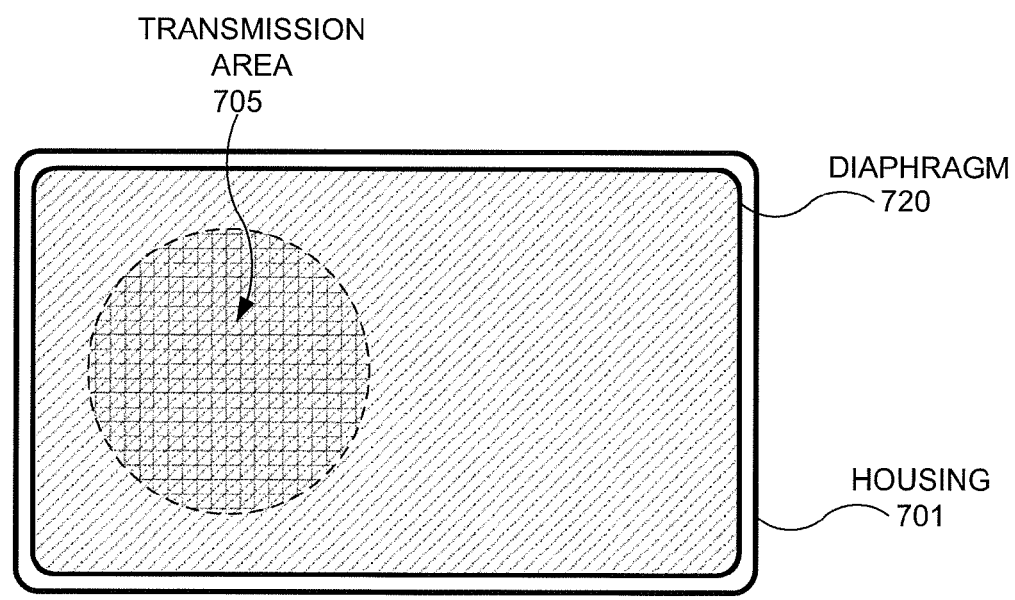
FIG. 8  *MEDICAL ASSIST DEVICE DETAIL*

COMPONENTS OF MEDICAL DEVICE WITH
EXTERIOR SPEAKER DIAPHRAGM

MEDICAL DEVICE WITH SPEAKER HAVING EXTERIOR DIAPHRAGM

CROSS REFERENCE TO RELATED PATENT APPLICATIONS

This patent application claims priority from U.S.A. Provisional Patent Application Ser. No. 61/385,501 entitled MEDICAL DEVICE WITH SPEAKER HAVING EXTERIOR MEMBRANE, filed on Sep. 22, 2010, the disclosure of which is hereby incorporated by reference for all purposes.

FIELD

This application generally relates to medical devices.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a lifesaving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrhythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

Advanced medical devices can actually coach a rescuer who performs CPR. For example, a medical device can issue instructions, and even prompts, for the rescuer to perform CPR more effectively. To provide such instructions or audio prompts, these advanced medical devices may include a speaker. However, because these advance medical devices are often used in environments that expose the device to a variety of potential contaminates, such as body fluids, dirt, debris, etc., the speaker on the device often becomes covered with contaminants that can interfere with the operation of the speaker. Additionally, the speakers can be extremely difficult to clean. If the rescuer attempts to cover the speaker with her hand or another object during treatment, any auditory sounds are largely muffled, making them ineffective. Embodiments of the invention address these and other deficiencies in the prior art.

BRIEF SUMMARY

The present description gives instances of medical devices, systems, software and methods, the use of which may help overcome problems and limitations of the prior art.

In one embodiment, a medical device for use by a rescuer who is caring for a patient includes a substantially rigid housing having a transmission area, a component located within the housing for one of detecting a parameter of the patient and delivering therapy to the patient for caring for the patient, a voice coil located within the housing and positioned substantially adjacent to the transmission area in the housing, the voice coil for receiving an electrical audio signal and for generating a preliminary sound signal in response to the audio signal, and a diaphragm disposed in the housing at the transmission area to provide a watertight seal of the transmission area, the diaphragm integrally formed as a portion of the housing that surrounds the transmission area, and the diaphragm structured to generate in response to the preliminary sound signal a rescuer sound, i.e. a sound that can be heard by the rescuer.

An advantage over the prior art is that the medical devices discussed in this description includes features that prevent contaminants from infiltrating the housing of the device while providing a mechanism to provide clear auditory sounds to aid a rescuer in providing care to a patient. Additionally, the medical device described here includes exterior surfaces that are easy to clean.

These and other features and advantages of this description will become more readily apparent from the following Detailed Description, which proceeds with reference to the drawings, in which:

BRIEF DESCRIPTION OF THE DRAWINGS

FIG. 1 is a block diagram of a medical device with a speaker having an exterior diaphragm according to embodiments.

FIG. 2 is a cross-sectional view of an exemplary medical device according to embodiments.

FIG. 3 is a cross-sectional view of another exemplary medical device according to embodiments.

FIG. 4 is a cross-sectional view of yet another exemplary medical device according to embodiments.

FIG. 5 is a diagram of a scene where the medical device shown in FIG. 1 is used to provide care to a patient according to embodiments.

FIG. 6 is another diagram of the scene shown in FIG. 5 where the medical device is used to aid in CPR care of a patient according to embodiments.

FIG. 7 is a diagram of an example of the medical device shown in FIG. 1 showing an exemplary position of an exterior diaphragm according to embodiments.

FIG. 8 is a diagram of another example of the medical device shown in FIG. 1 showing another exemplary position of an exterior diaphragm according to embodiments.

DETAILED DESCRIPTION

Figure 9:
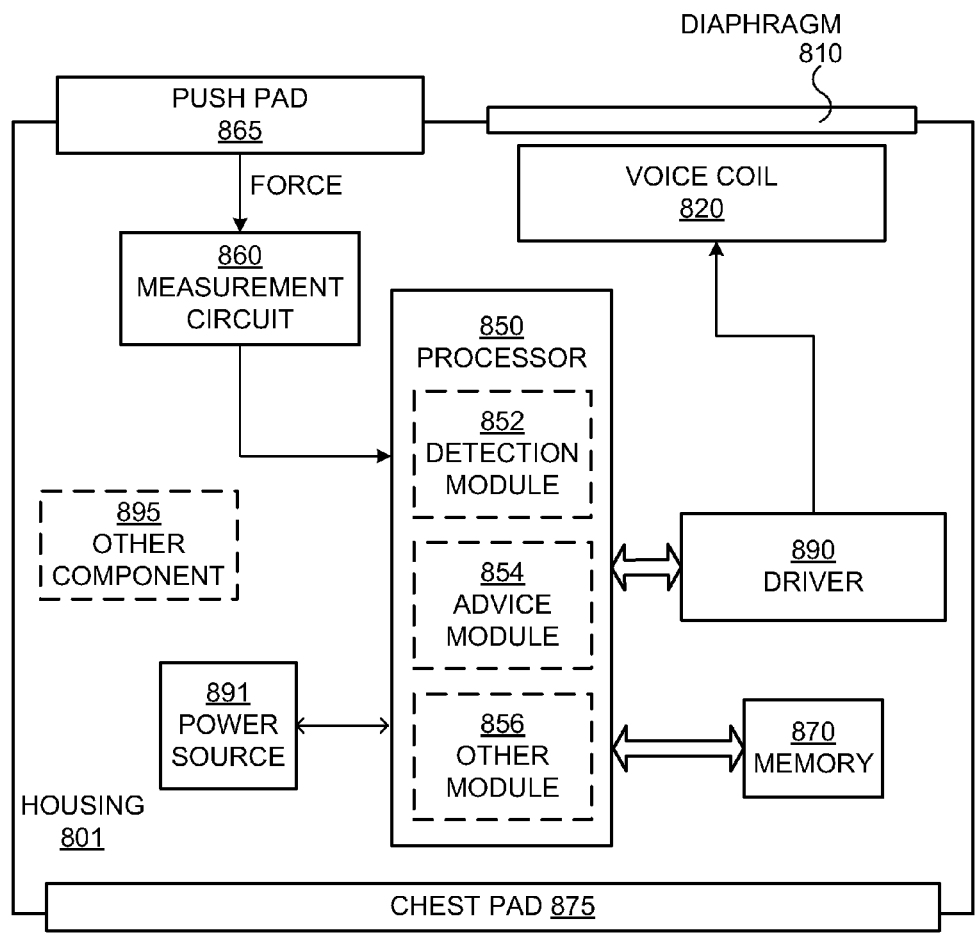
FIG. 9 is a block diagram of components of an exemplary medical device showing additional components according to embodiments.

As has been mentioned, the present description is about medical devices, control systems, software and methods for providing auditory instructions or prompts to a rescuer providing care to a patient.

Embodiments are now described in more detail.

FIG. 1 is a block diagram of a medical device for use by a rescuer who is caring for a patient. The medical device includes a substantially rigid housing 101.

The medical device encloses, within housing 101, a component 111 for caring for the patient. The component 111 either detects a parameter of the patient, or delivers therapy to the patient, according to what the medical device is intended for.

Also included within the housing 101 is a voice coil 120 for receiving an electrical audio signal, and for generating a preliminary sound signal in response to the audio signal. The housing 101 has a transmission area 105 for transmitting sound signals through the housing to be heard by the rescuer. The voice coil 120 is positioned substantially adjacent to the transmission area 105 in the housing. A diaphragm 110 is disposed in the housing 101 at the transmission area 105 to provide a watertight seal of the transmission area. To accomplish this watertight seal, the diaphragm 110 is preferably integrally formed as a portion of the housing that surrounds the transmission area. The diaphragm 110 is also structured to generate a rescuer sound 112 in response to the preliminary sound signal from the voice coil 120. For purposes of this document a rescuer sound 112 is a sound that can be heard directly by the rescuer, i.e. it is such that it does not need amplification by another component, before reaching the ears of the rescuer.

The rescuer sound 112 generated by diaphragm 110 can include various auditory sounds or instructions to aid the rescuer in caring for the patient. In one embodiment the auditory sounds include tones arranged at defined intervals, to provide cues as to actions the rescuer should take in caring for the patient. For example, if the medical device is structured to aid a rescuer in providing CPR to a patient, the auditory tones may signal to the rescuer when chest compressions should be administered, to ensure that they are completed at an optimum rate. In other embodiments, the auditory sounds include verbal instructions to provide the rescuer with procedures or tips in caring for the patient. In another CPR example, the verbal instructions may include both cues as to when to administer chest compressions, and when to provide breathing assistance. The verbal instructions may also provide instructions on CPR technique. In some embodiments, a medical device may be configured to provide both auditory tones and verbal instructions via the diaphragm 110. Here, the user may be able to switch between modes of receiving auditory sounds or these sounds may both be used to help the rescuer.

In rescuer sound 112 tests, an average rescuer sound level of about 64 to 68 dBA SPL (decibels with A weighting factor for sound pressure levels) was generated at about 50 cm from the diaphragm 110 for 600 Hz to 3400 Hz sound waves. These levels are higher than the dB levels for normal conversation, which generally range in the 40 dB to 60 dB range. However, because of the possible environmental noises associated with rescuing a person as well as possible elevated stress levels of the rescuer, the higher decibel levels may be favorable to ensure that the rescuer can hear them properly and accurately. Although these tests focused on a specific decibel range, lower or higher decibel ranges are possible. In some embodiments, the medical device may include a volume adjustment mechanism (not shown) to allow the user to increase or decrease the volume or decibel level of the rescuer sound 112.

In addition to being structured to generate a sound heard by a rescuer, the diaphragm 110 also provides a watertight seal with the housing 101. Since the medical device is often used in harsh environments, the diaphragm also should stand up the rigors or rough handling and be easy to clean. Thus, the material used for the diaphragm 110 should be flexible enough to provide auditory sounds, but also be durable enough to withstand use in the field. Example materials that may be used in or as the diaphragm 110 include Lexan 8B35V, Autotex Polyester EBA187L TS, and Valox FR1. These materials may be used alone, in combination with each other, or with other materials.

FIG. 2 is a cross-sectional view of an exemplary medical device according to embodiments. Here, the medical device includes a speaker cone 230 along with a voice coil 220 in a transmission area 205 of a substantially rigid housing 201. A diaphragm 210 is positioned in the transmission area 205 and is sealed to the housing 201 with one or more watertight air seals 215.

In this embodiment, the speaker cone 230 operates as a primary diaphragm to produce an initial audio sound, and the exterior diaphragm 210 disposed in the transmission area 205 of the housing 201 operates as a secondary diaphragm to produce the sound that can be heard by the rescuer from the initial audio sound. That is, the voice coil 220 generates a preliminary audio signal that moves the speaker cone 230 to produce the initial audio sound. This initial audio sound is then used by the exterior diaphragm 210 to generate the rescuer sound. For instance, air or another medium within the transmission area 205 may transfer energy from the movement of the voice coil 220 and cone 230 to the diaphragm 210.

The air seals 215 integrally attach the diaphragm 210 to an outside surface of the housing 201. In some embodiments the air seals 215 include an adhesive to form this integral attachment between the diaphragm 210 and housing 201. The adhesive may include a water-proof epoxy, glue, or other type of adhesive that provides and airtight and watertight seal around the transmission area 205.

FIG. 3 is a cross-sectional view of another exemplary medical device according to embodiments. Here, the medical device again includes a speaker cone 330 along with a voice coil 320 in a transmission area 305 of a substantially rigid housing 301. A diaphragm 310 is positioned in the transmission area 305 and is sealed to the housing 301 with at least one diaphragm clamp 308.

In this embodiment, the medical device also includes a structural element 340 attached to the housing 301, covering the transmission area 305 at least in part, and positioned between the voice coil 320 and the diaphragm 310. This structural element 340 is made of a substantially rigid material to protect the voice coil 320 and speaker cone 330 from external contact through the diaphragm 310 without overly interfering with the sound generation of the diaphragm. The structural element 340 may include multiple openings, as in a grill, so that the initial audio sound produced by the speaker cone 330 can still be transmitted to the diaphragm 310 to generate the sound heard by the rescuer. The structural element or grill 340 may be structured to be concave relative to the housing 301 to provide space for the diaphragm 310 to flex and generate the sound heard by the rescuer. In some embodiments, the structural element 340 may be made out of the same material as the housing 301.

The diaphragm clamp 308 may be configured to attach the diaphragm 310 to an outside surface of the housing 301 and providing a watertight seal between the diaphragm and housing. The diaphragm clamp 308 may include a continuous edge that presses and holds end portions of the diaphragm 310 in place thereby creating the watertight seal and integral formation of the diaphragm. The diaphragm clamp 308 may include a number of fastener holes that allow the clamp or clamps to be tightened down to the housing 301 to hold the diaphragm 310. Alternatively, the diaphragm clamps 308 may include one or more buckles, levers, or other tightening systems to hold and seal the diaphragm 310. One advantage of the diaphragm clamp 308 system is that if the diaphragm 310 becomes damaged, it may be easily removed and replaced with a new diaphragm. The diaphragm clamps 308 may also be structured so that a top surface of the diaphragm 310 is substantially coplanar with a top surface the clamp 308. By having the top surfaces substantially coplanar, the device may be easier to clean and contaminants may have less places to remain after cleaning the device.

FIG. 4 is a cross-sectional view of yet another exemplary medical device according to embodiments. Here, the medical device includes a voice coil 420 and magnet 425 in a transmission area 405 of a substantially rigid housing 401, but, different from the medical device of FIG. 3, does not include a separate speaker cone. A diaphragm 410 is positioned in the transmission area 405 and is sealed to the housing 401.

In this embodiment, the voice coil 420 is directly coupled to the diaphragm 410 so that the diaphragm is structured to operate as a primary diaphragm for the voice coil 420 to produce the sound that can be heard by the rescuer. That is, the voice coil 420 generates a preliminary audio signal that moves the exterior diaphragm 410 to generate the sound heard by the rescuer.

FIG. 5 is a diagram of a scene where the medical device 500 shown in FIG. 1 is used to provide care to a patient 582 according to embodiments. Here, the patient 582 is lying on their back. Patient 582 could be a patient in a hospital, or someone found unconscious, and then turned to be on their back. Patient 582 is experiencing a condition in their heart 585, which could be Ventricular Fibrillation (VF). The medical device 500 is positioned near the heart 585 of the patient 582 to provide the needed care.

FIG. 6 is another diagram of the scene shown in FIG. 5 where the medical device 500 is used to aid in CPR care of a patient 582 according to embodiments. Here, the medical device 500 includes a housing 501 and diaphragm 520. To provide care to the patient 582, the medical device 500 may need to be placed in a particular region of the person's chest. The housing 501 may include visual cues so that the medical device 500 can be aligned with a nipple line 590 of the patient 582 corresponding to a line that passes over both of the nipples 586 of the patient 582. The diaphragm 520 may also provide verbal instructions to the rescuer on how to position the medical device 500 to provide the best care for the patient 582.

FIG. 7 is a diagram of an example of the medical device shown in FIG. 1 showing an exemplary position of an exterior diaphragm 620 according to embodiments. Here, the diaphragm 620 is only slightly larger than the transmission area 605 of the housing 601 that the diaphragm seals.

FIG. 8 is a diagram of another example of the medical device shown in FIG. 1 showing another exemplary position of an exterior diaphragm 720 according to embodiments. Here, the diaphragm 720 is much larger than the transmission area 705 of the housing 701 that the diaphragm seals. The diaphragm 720 may in fact cover an entire surface of the medical device. Various other sizes and positions of the diaphragm are possible in other embodiments, as well.

FIG. 9 is a block diagram of components of an exemplary medical device showing additional components according to embodiments. Here, the housing 801 of the medical device includes a processor 850 that is connected to a driver 890 that drives the voice coil 820 positioned adjacent to the exterior diaphragm 810 used to generate a sound to aid a rescuer in providing care to a patient. The driver 890 located in the housing 801 may be configured to provide the electrical audio signal to the voice coil in response to signals received from the processor 850. The processor 850 may provide these signals based on a set protocol stored in a coupled memory 870, or may provide them based on feedback received from a push pad 865 or chest pad 875. For example, a measurement circuit 860 may detect the pressure applied to the push pad 865 and send a signal to a detection module 852 in the processor 850. The detection module may interpret the pressure and compare it to known values. An advice module 854 in the processor 850 may then provide signals to the driver 890 to provide auditory feedback to the rescuer via the diaphragm 810. Some of the functions of the medical device may be controlled by software or embedded firmware that provide instructions on operational functions in response to predefined conditions or detected inputs.

The housing 801 may also include a power source 891 to power the internal components of the medical device. In some embodiments, the medical device may include other components 895, such as a defibrillator to provide additional care to the patient. In these embodiments, the processor 850 may include other modules 856 to operate these other components 895. In some of these embodiments, the medical device may also monitor a vital sign of the patient and provide advices to the rescuer on performing CPR chest compressions through auditory instructions provided via the diaphragm 810 or on a visual display (not shown). In yet other embodiments, the medical device may automatically perform chest compressions on the patient once properly aligned on the patient by the rescuer.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and subcombinations of elements, features, steps, and/or functions, which are regarded as novel and non-obvious. Additional claims for other combinations and subcombinations may be presented in this or a related document.

What is claimed is:

1. A medical device for use by a rescuer who is caring for a patient, comprising:
    a substantially rigid housing having a transmission area;
    a component located within the housing configured to detect a parameter of the patient or deliver therapy to the patient or both;
    a voice coil located within the housing and positioned substantially adjacent to the transmission area, the voice coil configured to generate a preliminary sound signal in response to an electrical audio signal;
    an exterior diaphragm to provide a watertight seal of the transmission area, the exterior diaphragm integrally formed as a portion of the housing that surrounds the transmission area, and the exterior diaphragm structured to generate in response to the preliminary sound signal a rescuer sound that can be heard directly by the rescuer; and
    a structural element directly attached to the housing, covering the transmission area at least in part, and disposed between the voice coil and the exterior diaphragm.

2. The medical device of claim 1, further comprising a speaker cone located in the housing and connected to the voice coil.

3. The medical device of claim 2, in which the speaker cone operates as a primary diaphragm to produce an initial audio sound, and in which the exterior diaphragm disposed in the transmission area of the housing operates as a secondary diaphragm to produce the rescuer sound from the initial audio sound.

4. The medical device of claim 1, further comprising a driver located in the housing and coupled to the component and voice coil, the driver configured to provide the electrical audio signal to the voice coil.

5. The medical device of claim 4, in which the driver is configured to provide the electrical audio signal to the voice coil in response to signals received from the component.

6. The medical device of claim 1, in which in the exterior diaphragm is attached to an outside surface of the housing with an adhesive.

7. The medical device of claim 1, in which the exterior diaphragm is attached to an outside surface of the housing with at least one clamp.

8. The medical device of claim 7, in which a top surface of the external diaphragm is substantially coplanar with a top surface of the at least one clamp.

9. The medical device of claim 1, in which the exterior diaphragm includes at least one of Lexan 8B35V, Autotex Polyester EBA187L TS, and Valox FR1.

10. The medical device of claim 1, in which the component includes a processor.

11. The medical device of claim 1, in which the exterior diaphragm is further structured to generate in response to the preliminary sound signal a rescuer sound of at least 64 dBA SPL at 50 cm from the exterior diaphragm.

* * * * *